United States Patent
Glauser et al.

(10) Patent No.: US 9,421,223 B2
(45) Date of Patent: *Aug. 23, 2016

(54) NITRIC OXIDE GENERATING MEDICAL DEVICES

(71) Applicant: Abbott Cardiovascular Systems Inc., Santa Clara, CA (US)

(72) Inventors: Thierry Glauser, Redwood City, CA (US); Stephen D. Pacetti, San Jose, CA (US); Paul M. Consigny, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/622,131

(22) Filed: Feb. 13, 2015

(65) Prior Publication Data

US 2015/0157658 A1   Jun. 11, 2015

Related U.S. Application Data

(60) Continuation of application No. 13/923,559, filed on Jun. 21, 2013, now Pat. No. 8,986,724, which is a continuation of application No. 13/276,666, filed on Oct. 19, 2011, now Pat. No. 8,470,358, which is a division of application No. 11/726,135, filed on Mar. 20, 2007, now Pat. No. 8,067,025, which is a division of application No. 11/356,696, filed on Feb. 17, 2006, now abandoned.

(51) Int. Cl.
| | |
|---|---|
| *A61L 29/16* | (2006.01) |
| *A61L 31/08* | (2006.01) |
| *A61K 33/00* | (2006.01) |
| *A61L 31/16* | (2006.01) |
| *A61K 45/06* | (2006.01) |
| *A61L 31/10* | (2006.01) |
| *A61L 31/14* | (2006.01) |

(52) U.S. Cl.
CPC ............... *A61K 33/00* (2013.01); *A61K 45/06* (2013.01); *A61L 29/16* (2013.01); *A61L 31/08* (2013.01); *A61L 31/10* (2013.01); *A61L 31/148* (2013.01); *A61L 31/16* (2013.01); *A61L 2300/114* (2013.01); *A61L 2300/606* (2013.01)

(58) Field of Classification Search
CPC .............................. A61L 31/00; A61L 24/04
USPC ...................... 424/78.27, 422, 423
See application file for complete search history.

(56) References Cited

U.S. PATENT DOCUMENTS

| | | | |
|---|---|---|---|
| 4,733,665 A | 3/1988 | Palmaz | |
| 4,800,882 A | 1/1989 | Gianturco | |
| 4,882,168 A | 11/1989 | Casey et al. | |
| 4,886,062 A | 12/1989 | Wiktor | |
| 5,676,963 A | 10/1997 | Keefer et al. | |
| 5,797,887 A | 8/1998 | Rosen et al. | |
| 6,171,232 B1 * | 1/2001 | Papandreou | ........ A61L 33/0076 424/423 |
| 6,232,434 B1 | 5/2001 | Stamler et al. | |
| 6,270,779 B1 | 8/2001 | Fitzhugh et al. | |
| 6,541,116 B2 | 4/2003 | Michal et al. | |
| 7,008,667 B2 | 3/2006 | Chudzik et al. | |
| 8,067,025 B2 | 11/2011 | Glauser et al. | |
| 8,470,358 B2 | 6/2013 | Glauser et al. | |
| 8,986,724 B2 | 3/2015 | Glauser et al. | |
| 2002/0055666 A1 | 5/2002 | Hunter et al. | |
| 2002/0115559 A1 | 8/2002 | Batchelor et al. | |
| 2002/0146557 A1 | 10/2002 | Claude et al. | |
| 2003/0088307 A1 | 5/2003 | Shulze et al. | |
| 2004/0044405 A1 | 3/2004 | Wolff et al. | |
| 2004/0224868 A1 | 11/2004 | Meyerhoff et al. | |
| 2006/0013853 A1 | 1/2006 | Richard | |
| 2006/0039950 A1 | 2/2006 | Zhou et al. | |
| 2006/0067908 A1 | 3/2006 | Ding | |
| 2007/0196428 A1 | 8/2007 | Glauser et al. | |
| 2009/0118819 A1 | 5/2009 | Merz et al. | |
| 2009/0188819 A1 * | 7/2009 | Carney, Jr. | ........... A47B 43/003 206/315.1 |

FOREIGN PATENT DOCUMENTS

| | | |
|---|---|---|
| WO | WO 98/08482 | 3/1998 |
| WO | WO 00/02501 | 1/2000 |
| WO | WO 02/056904 | 7/2002 |
| WO | WO 2004/060283 | 7/2004 |
| WO | WO 2005/094913 | 10/2005 |
| WO | WO 2007/097875 | 8/2007 |

OTHER PUBLICATIONS

U.S. Appl. No. 11/437,075, filed May 18, 2006, Trollsas et al.
International Search Report for PCT/US2007/002124, mailed Mar. 5, 2008, 16 pgs.
European Search Report for 07717041.3, mailed Feb. 19, 2009, 6 pgs.
Benkeser et al., "Factors governing orientation in metalation reactions. II. The metalation of isopropylbenzene with n-amylsodium and n-amylpotassium", J. of Am. Chem. Soc. vol. 85, pp. 3984-3989 (1963).
Bryce-Smith "Organometallic compounds of the alkali metals. Prat VII. Orientation in protophilic aromatic metallation by ethylsodium and ethyl—lithium—potassium reagents: Factors influencing the reactivity of metallating reagents", J. of the Chem. Soc. GB pp. 5983-5991 (1963).
Bryce-Smith "The hydrogen isotope effect in the metallation of benzene and toluene", J. of the Chem. Soc. GB pp. 2743-2747 (1954).
Ewing et al., "Nitrosylated Bovine Serum Albumin Derivatives as Pharmacologically Active Nitric Oxide Congeners", J. of Pharm. and Exper. Therapeutics 283, pp. 947-954 (1997).
Frost et al., "Polymers incorporating nitric oxide releasing/generating substances for improved biocompatibility of blood-contacting medical devices", Biomaterials 26, pp. 1685-1693 (2005).

(Continued)

*Primary Examiner* — Michael G Hartley
*Assistant Examiner* — Jagadishwar Samala
(74) *Attorney, Agent, or Firm* — Squire Patton Boggs (US) LLP

(57) ABSTRACT

Medical devices having a catalyst capable of catalyzing the generation of nitric oxide in vivo and methods of treating a vascular condition using the devices are provided.

20 Claims, No Drawings

(56) References Cited

OTHER PUBLICATIONS

Lindberg et al., "Nitric Oxide Gives Maximal Response After Coronary Artery Bypass Surgery", J. of Cardiothoracic and Vascular Anesthesia, vol. 8, No. 2, pp. 182-187 (1994).

Miyaura et al., "Palladium-catalyzed cross-coupling reaction of organoboron compounds", Chemical Review 95, pp. 2457-2483 (1995).

Oh et al., "Spontaneous Catalystic Generation of Nitric Oxide From S-Nitrosothiols at the Surface of Polymer Films Doped with Lipophilic Copper (II) Complex", J. Am. Chem. Soc. 125: pp. 9552-9553 (2003).

Oh et al.,"Catalytic generation of nitric oxide from nitrite at the interface of polymeric films doped with lipophilic Cu(II)-complex: a potential route to the preparation of thromboresistant coatings", Biomat. 25, pp. 283-293 (2004).

Pocker et al., "Deuterium isotope effects in the decomposition of organometals by proton donors", J. of the Am. Chem. Soc. 90:24, pp. 6764-6773 (1968).

Sakharov et al., "Polylysine as a Vehicle for Extracellurar Matrix-Targeted Local Delivery, Providing High Accumulation Long-Term Retention Within the Vascular Wall", Arterioscler Thromb. Vasc. Biol. pp. 943-948 (2001).

Wang et al. Design and Synthesis of Metal Ion-Recognition-Induced Conjugated Polymers: An Approach to Metal Ion Sensory Materials, JACS, 1997, vol. 119, pp. 12-21.

\* cited by examiner

NITRIC OXIDE GENERATING MEDICAL DEVICES

RELATED APPLICATIONS

This application is a continuation of U.S. patent application Ser. No. 13/923,559, filed on 21 Jun. 2013 (published as U.S. Pat. App. Pub. No. US 2013-0287833 A1 on 31 Oct. 2013, and issuing as U.S. Pat. No. 8,986,724 B2 on 24 Mar. 2015), which was a continuation of U.S. patent application Ser. No. 13/276,666, filed on 19 Oct. 2011 (published as U.S. Pat. App. Pub. No. 2012-0034222 A1 on 9 Feb. 2012, and issuing as U.S. Pat. No. 8,470,358 on 25 Jun. 2013), which application was a divisional application of U.S. patent application Ser. No. 11/726,135, filed on 20 Mar. 2007 (issuing as U.S. Pat. No. 8,067,025 on 29 Nov. 2011), which application was a divisional application of U.S. patent application Ser. No. 11/356,696, filed on 17 Feb. 2006 (published as U.S. Pat. App. Pub. No. 2007-0196428 A1 on 23 Aug. 2007, and now abandoned), all of which are incorporated by reference in their entirety as if fully set forth herein.

FIELD

This invention is generally related to medical devices capable of in vivo generation of nitric oxide.

BACKGROUND

Stents are used not only as a mechanical intervention in vascular conditions but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents that have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects on the patient. Local delivery is a preferred method of treatment in that smaller total levels of medication are administered in comparison to systemic dosages, but are concentrated at a specific site. Local delivery thus produces fewer side effects and achieves more favorable results.

In many patients, especially diabetic patients, stentable lesions are focal manifestations of widespread vascular disease. The advent of drug delivery stents has brought relief from restenosis of the treated lesion, but leaves progression of regional vascular disease unaddressed.

Nitric oxide (NO) has numerous physiologic and pathophysiologic functions. For example, NO can inhibit the inflammatory process by lowering cytokine synthesis and inactivating nuclear factor (NF)-κB,3 as several cytokines contain a binding site for NF-κB in their promoter regions. It has been reported that blood level NO can inhibit platelet adhesion and aggregation, inflammation, and smooth muscle cell migration and proliferation and can stimulate endothelial cell migration and proliferation. In addition, NO has vasorelaxant effect and can regulate smooth muscle contractility and platelet reactivity (see, e.g., Lindberg, L., et al., Nitric Oxide gives maximal response after coronary artery bypass surgery. J. Cardiothorac Vasc. Anesth. 8:182-87 (1994)).

Therefore, the present invention provides means of generating nitric oxide to cure the deficiencies of a conventional drug delivery stent.

SUMMARY

A medical device is provided comprising a polymer and a metal complex attached to the polymer, wherein the metal complex catalyzes the generation of nitric oxide in the blood stream or in tissue adjacent to the medical device. In some embodiments, the polymer is included in a coating for the medical device. In some embodiments, the medical device is a bioabsorbable stent made from at least the polymer. The metal complex can be a copper complex. The metal complex can comprise Cyclen, Cyclam, DTTCT, or a bipyridine ligand. The metal complex can be attached to the polymer with a spacer. The spacer can be a short-chain alkyl group, phenyl group, an aryl group, or poly(ethylene glycol). In some embodiments, the metal complex comprises a metal selected from the group consisting of $Cu^{2+}$, $Co^{2+}$, $Ni^{2+}$, $Zn^{+2}$, $Mn^{2+}$, $Al^{3+}$, or $Fe^{3+}$. The medical device can include a drug adapted to be released from the device. The drug can be included in a coating. The coating can be made from the polymer to which the complex is attached. The nitric oxide can be released from a nitrosylated biomolecule present in the blood stream or a tissue adjacent to the medical device. The nitric oxide can be released from a nitrosylated protein or S-nitrosothiols present in the blood stream or in tissue adjacent to the medical device.

In accordance with another aspect of the invention, a medical device comprising a metal complex is provided, wherein the metal complex is attached to the surface of the medical device or a coating on the medical device, and wherein the metal complex catalyzes the generation of nitric oxide in the blood stream or in tissue adjacent to the medical device.

DETAILED DESCRIPTION

The present invention provides methods for generating NO in blood. According to embodiments of the present invention, NO can be released from a nitric oxide source present in the blood stream or a tissue when the nitric oxide source meets a metal catalyst in the blood stream or the tissue. The metal catalyst can be attached to a coating (e.g., a topcoat) on a medical device with a spacer. Upon exposure to the blood stream or the tissue, the metal catalyzes the release of NO from the NO source. The nitric oxide source can comprise nitrosylated biomolecules such as nitrosylated proteins (e.g., S-nitrosothiols).

NO has numerous physiologic and pathophysiologic functions. For example, NO can inhibit the inflammatory process by lowering cytokine synthesis and inactivating nuclear factor (NF)-κB,3 as several cytokines contain a binding site for NF-κB in their promoter regions. It has been reported that blood level NO can inhibit platelet adhesion and aggregation, inflammation, and smooth muscle cell migration and proliferation and can stimulate endothelial cell migration and proliferation. In addition, NO has vasorelaxant effect and can regulate smooth muscle contractility, and platelet reactivity.

The metal catalyst includes a metal, which can be a metal ion or a metal atom, and one or more ligands. The ligand can have two or more coordination sites. Preferably, the ligand has four nitrogen atoms that serve as coordination sites in the ligand. The metal catalyst can be formed prior to the ligand's attachment to a polymer coating or after the ligand's attachment to the polymer coating. Preferably, the catalyst is formed after the ligand's attachment to the coating.

In some embodiments, a coating including the metal complex described herein can be formed directly on the surface of a medical device or on top of a layer of a coating that includes a biocompatible polymer. In some embodiments, the coating can be formed on top of a drug reservoir, which can be a layer of neat or pure drug(s) or a layer that includes a biocompatible polymer combined with a drug or combination of drugs.

In some embodiments, the medical device itself can be bioabsorbable (e.g., a bioabsorbable stent) and the catalyst can be attached directly to the surface of the device. In some embodiments, the catalyst can also be attached to a coating of the bioabsorbable device.

The medical device having the catalyst described herein can include one or more biocompatible polymer(s) and optionally one or more biobeneficial material(s). In some embodiments, the coating can include a bioactive agent such as a drug. Some examples of the bioactive agents include, but are not limited to, paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N-1-tetrazolyl)-rapamycin (ABT-578), pimecrolimus, imatinib mesylate, midostaurin, clobetasol, bioactive RGD, CD-34 antibody, abciximab (REOPRO), progenitor cell capturing antibody, prohealing drugs, prodrugs thereof, co-drugs thereof, or a combination thereof.

The medical device including a catalyst described herein can be used to treat, prevent, or ameliorate a vascular medical condition such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

Metal Complexes

Copper complexes have been shown to generate biologically relevant levels of NO for up to 6 hours (see, e.g., Oh, B. K. and Meyerhoff, M. E., *Biomaterials* 25:283-293 (2005)). NO generation occurs as long as the copper catalyst is present and a nitrosylated biomolecule (e.g., nitrosylated proteins or S-nitrosothiols) in the blood reaches the copper catalyst (see, e.g., Oh, B. H., Meyerhoff, M. E., *J. Amer. Chem. Soc.*, 125(32):9552-53) (2003). NO generation can be achieved when a metal ion (e.g., copper or zinc) is bound to a ligand such as Cyclen (see Scheme I), Cyclan (see Scheme I), or macrocycles having four nitrogen groupings. One such macrocycle ligand is dibenzo[e,k]-2,3,8,9-tetraphenyl-1,4,7,10-tetraaza-cyclododeca-1,3,7,9-tetraene (DTTCT). The electronic and steric environment provided by the ligands influences the metal ion's reactivity and selectivity. Therefore, it is important not to significantly modify the structure of the macrocycle in attaching the ligand to a polymer in the coating on a medical device.

The metal catalyst can be any metal complex capable of catalyzing the generation of nitric oxide in the blood stream or the tissue. In some embodiments, the metal complex is a copper complex. In some embodiments, the metal complex contains a metal such as $Co^{2+}$, $Ni^{2+}$, $Zn^{+2+}$, $Mn^{2+}$, $Al^{3+}$, or $Fe^{3+}$.

The metal complex can be formed by mixing a metal compound and the ligand described herein and allowing the ligand to complex with the metal. Methods for forming a metal complex are well documented in the art. Some references can be found in A.B.P. Lever, Editor-in-Chief, *Coordination Chemistry Reviews*, published by Elsevier.

Ligands useful for forming the metal complex described herein are chelating ligands having multiple coordination sites. The ligands can have at least two coordination sites, preferably three coordination sites, more preferably four coordination sites. In some embodiments, the ligand is an N4 macrocycle ligand (a ligand having four nitrogen coordination sites). Some representative N4 ligands include, but are not limited to, Cyclen, Cyclam, and DTTCT.

In some embodiments, the ligand can have two coordination sites. Two or more equivalents of the ligands can complex to a metal to form a metal complex. For example, two equivalents of an N2 ligand (ligand having two nitrogen coordination sites) can complex to a metal such as copper to form a metal complex having four nitrogen coordination sites. Some representative N2 ligands are, for example, 2,2'-bipyridine ligands.

Standard procedures can be used to introduce the metal (e.g., a metal ion) into the macrocycle.

To have a local generation of NO, in some embodiments, the metal complex described herein is attached to the surface of a medical device or a coating on the device through a spacer. The spacer can be, for example, an alkyl chain or a poly(ethylene glycol) (PEG) chain. The spacer has a length of at least two carbon atoms or longer. This can allow the copper complex to be at the blood polymer interface and have the active center accessible to nitrosylated biomolecules (e.g., nitrosylated proteins or nitrosothiols) in the blood. The metal complex can either be coupled to the spacer and then to the polymer or coupled to a spacer that is already attached to the polymer. The order of the reactions is dictated by the compatibility of the chemistry, which can be readily appreciated by one of ordinary skill in the art.

Exemplary spacers that can be used in the present invention include, but are not limited to, PEG, poly(alkylene oxide) such as poly(ethylene oxide) (PEO) and poly(propylene oxide) (PPO), C2-C20 alkyls, and short peptides. In some embodiments, the spacer can be a biocompatible polymer or oligomer.

Synthesis and/or Functionalization of Ligands

Attachment of a spacer to ligands can be achieved by functionalizing the ligand and then coupling the functionalized ligand to a spacer. Functionalization of the ligand can be carried out using standard procedures in organic synthesis. To illustrate, Cyclen and Cyclam, both having N—H groups in their molecules, can be coupled to a spacer that has a leaving group such as a halo group and a reactive group R, which can be any reactive group such as carboxyl, hydroxyl, thiol, or amine groups (Scheme I). The reactive group can be used to attach Cyclen or Cyclam to the reactive groups available on the polymer.

Scheme I

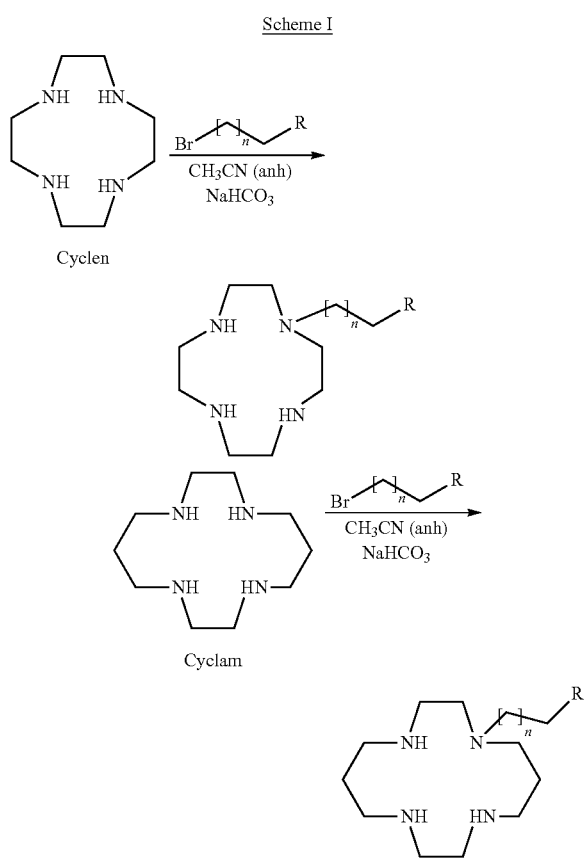

Cyclen

Cyclam

In some embodiments, the free reactive groups on a ligand (such as N—H groups on Cyclam) can be selectively protected by a protective group such as t-bock. The remaining reactive group can then be used to attach the ligand to a spacer. Other N4 macrocycles, such as DTTCT, can be synthesized to bear functional groups by selecting functionalized starting materials. As shown in Scheme II, two molecules of a diamine with an R1 group, which can have a protected functional group such as hydroxyl, amine or carboxylic acid group, can react with two molecules of a diketone having R2 groups to form a N4 macrocycle (Scheme II).

Scheme II

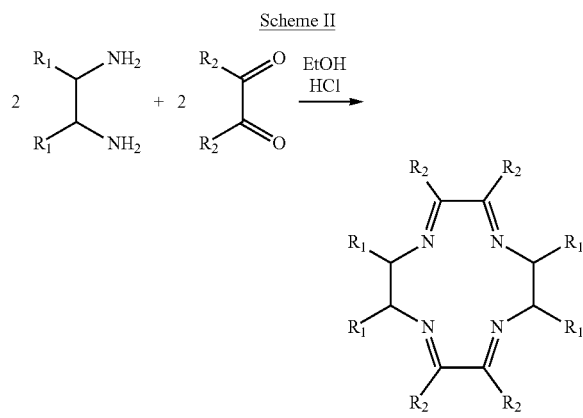

In Scheme II, where the diamine is 1,2-di-amine-benzene and the R2 group of the diketone is a phenyl group, the N4 macrocycle is DTTCT, which can form a copper complex as shown below:

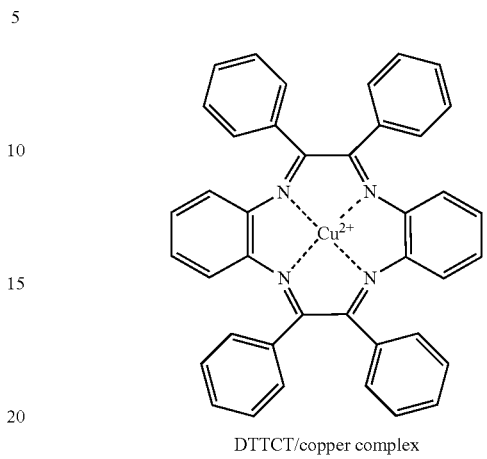

DTTCT/copper complex

Other methods for functionalizing macrocyclic ligands are well documented. For example, acylations of phenyls can be done by a Friedel-Crafts reaction (Bryce-Smith D. J.; *J. Chem. Soc.*, 1963, 5983, and Benkeser et al. *J. Am. Chem. Soc.* 1963, 85, 3984). Acyl halides (Bryce-Smith D. J. et al., J. Chem. Soc. 1954, 2743 and Pocker Y. et al. *J. Am. Chem. Soc.* 1968, 90, 6764) are the most common reagents, but carboxylic acids, anhydrides and ketenes can also be used. For example an acid chloride (RCOCl) can attack the hydrogen on the phenyl (R2 in Scheme II=phenyl) to yield ROCR2. Alternatively, a Suzuki coupling (Miyaura N. and Suzuki A., *Chem. Rev.* 1995, 95, 2457) can be performed between an organo-boronic acid and halides using a palladium catalyst. It is noteworthy that the Suzuki coupling is a milder reaction. In some embodiments, reactive groups on the ligand or the polymer may need to be protected (t-BOC, etc.) to avoid undesirable side reactions. In some embodiments, to obtain a single attachment point, less than 1 equivalent of acid chloride can be added. Subsequent purification can be needed.

Coupling of Spacer to Polymer

Coupling of spacers to a polymer in a coating or on the surface of a medical device can be achieved using two mechanisms. In some embodiments, the metal complex can be coupled to a polymer and then sprayed as a coating onto the medical device. In some embodiments, the polymer can be applied to the medical device and the metal complex can be subsequently coupled to the polymer coating. This approach can generate a coating having a higher surface density of the metal complex. The polymer should have reactive side groups such as hydroxyls, carboxylic acids, amines, etc. In some embodiments the medical device, such as a bioabsorbable polymer stent, can be made to include the metal complex.

In some embodiments, the polymer (e.g., coating or the device surface) has mildly reactive hydroxyl groups. The spacer should have reactive groups such as a carboxylic acid, N-hydroxysuccinimide (NHS), an acid halide (e.g., acid chloride) or equivalent thereof, or a vinyl sulphone. A carboxylic acid or NHS can be readily coupled to a hydroxyl group in the presence of N,N'-carbonyldiimidazole or dicyclohexylcarbodiimide (DCC), which are commercially available.

In some embodiments, the spacer can be poly(ethylene glycol) (PEG). PEG can be readily functionalized using acryloyl chloride to bear an acryloyl chloride end group. This end group can serve to couple PEG to the reactive groups on the polymer.

In some embodiments, the spacer can comprise vinyl sulphone, which can be readily coupled to the polymer under acidic conditions. Vinyl sulphone is commercially available.

As an example, Scheme III shows coupling of a copper complex to a hydroxyl functional methacrylate via a PEG spacer.

droxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone),

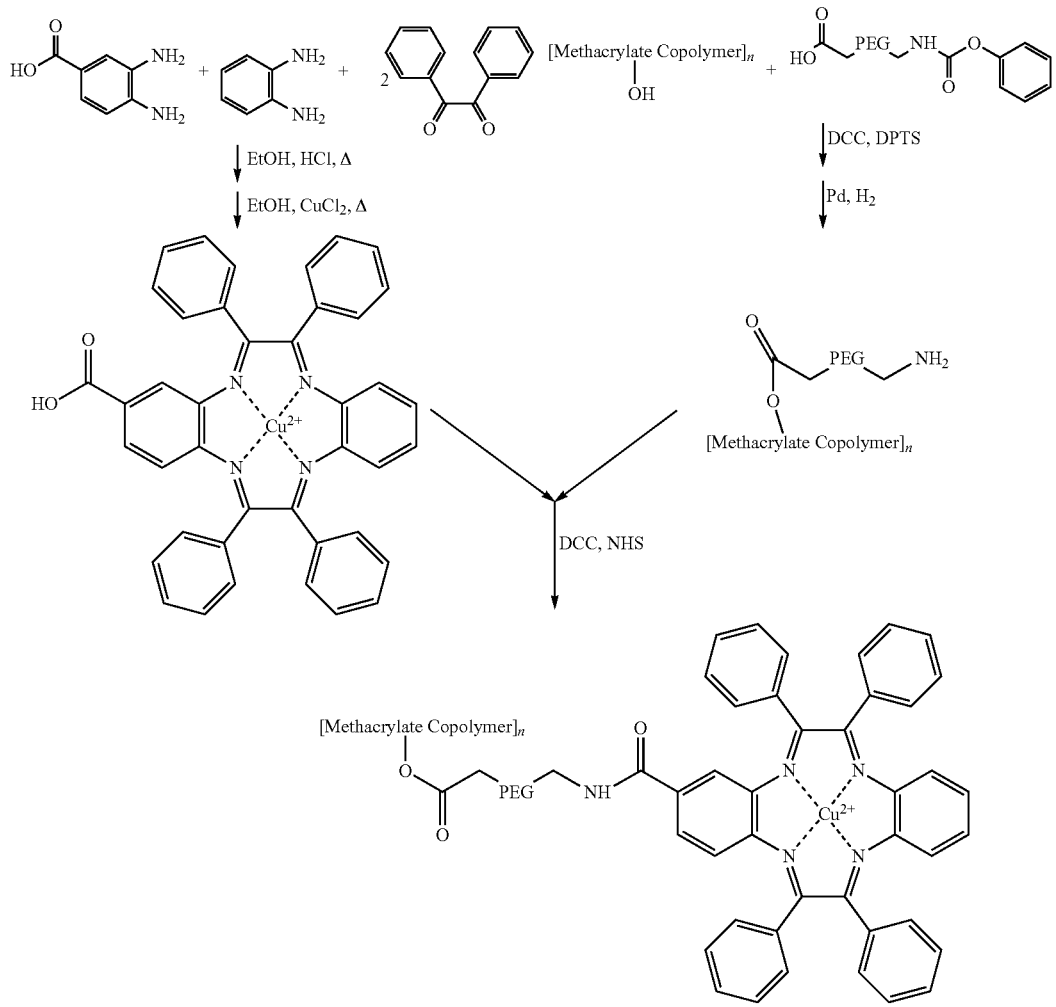

Scheme III

Biocompatible Polymers

A biocompatible polymer can be applied to a device and then coupled to the metal complex so as to form a coating. In some embodiments, the biocompatible polymer can be coupled with the metal complex, and afterwards be sprayed onto a device as a coating.

The biocompatible polymer can be biodegradable (either bioerodable or bioabsorbable or both) or nondegradable and can be hydrophilic or hydrophobic. Representative biocompatible polymers include, but are not limited to, poly(ester amide), polyhydroxyalkanoates (PHA), poly(3-hydroxyalkanoates) such as poly(3-hydroxypropanoate), poly(3-hypoly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide-co-lactic acid) (PEO/PLA)), polyalkylene oxides such as poly(ethylene oxide), poly(propylene oxide), poly(ether ester), polyalkylene oxalates, phosphoryl choline, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as collagen, chitosan, alginate, fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, elastin, or combinations thereof. In some embodiments, the topcoat can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly(D,L-lactic acid), poly(L-lactic acid), poly(D,L-lactic acid-co-glycolic acid), or poly(L-lactic acid-co-glycolic acid), respectively.

Bioactive Agents

The medical device having the metal complex described herein can include one or more bioactive agent(s), which can be therapeutic, prophylactic, or diagnostic agent(s). These agents can have anti-proliferative or anti-inflammatory properties or can have other properties such as antineoplastic, antiplatelet, anti-coagulant, anti-fibrin, antithrombogenic, antimitotic, antibiotic, antiallergic, and antioxidant. The agents can be cystostatic agents, agents that promote the healing of the endothelium such as NO releasing or generating agents, agents that attract endothelial progenitor cells, agents that promote the attachment, migration and proliferation of endothelial cells (e.g., natriuretic peptides such as CNP, ANP or BNP peptide or an RGD or cRGD peptide), while impeding smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Some other examples of the bioactive agent include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include 40-epi-(N1-tetrazolyl)-rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, or combinations thereof. Examples of cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, bioactive RGD, SIKVAV peptides, elevating agents such as cANP or cGMP peptides, and genetically engineered endothelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than non-therapeutic levels. The dosage or concentration of the bioactive agent can depend upon factors such as the particular circumstances of the patient, the nature of the trauma, the nature of the therapy desired, the time over which the administered ingredient resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Medical Device

As used herein, a medical device may be any suitable medical substrate that can be implanted in a human or veterinary patient. Examples of such medical devices include self-expandable stents, balloon-expandable stents, stent-grafts, grafts (e.g., aortic grafts), heart valve prostheses, cerebrospinal fluid shunts, electrodes, pacemaker electrodes, catheters, sensors, endocardial leads (e.g., FINE-LINE® and ENDOTAK®, available from Guidant Corporation, Santa Clara, Calif.), anastomotic devices and connectors, orthopedic implants such as screws, spinal implants, and electro-stimulatory devices. The underlying structure of the device can be of virtually any design. The device can be made of a metallic material or an alloy such as, but not limited to, cobalt chromium alloy (ELGILOY®), stainless steel (316L), high nitrogen stainless steel, e.g., BIODUR® 108, cobalt chrome alloy L-605, "MP35N," "MP20N," ELASTINITE® (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. In some embodiments, the device is a bioabsorbable stent, with or without a coating, such that the complex is attached to the coating or the surface of the device itself.

Method of Use

In accordance with embodiments of the invention, a medical device having the metal complex described herein can be used for the generation of nitric oxide in the blood stream or tissue adjacent to the medical device.

Preferably, the medical device is a stent. The stent described herein is useful for a variety of medical procedures, including, by way of example, treatment of obstructions caused by tumors in bile ducts, esophagus, trachea/bronchi and other biological passageways. A stent having the above-described coating is particularly useful for treating diseased regions of blood vessels caused by lipid deposition, monocyte or macrophage infiltration, or dysfunctional endothelium or a combination thereof, or occluded regions of blood vessels caused by abnormal or inappropriate migration and proliferation of smooth muscle cells, thrombosis, and restenosis. Stents may be placed in a wide array of blood vessels, both arteries and veins. In some embodiments, the device described herein can be in dialysis, as grafts, or fistulae.

Representative examples of sites include the iliac, renal, carotid and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described features may then be expanded at the desired area of treatment. A post-insertion angiogram may also be utilized to confirm appropriate positioning.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed:

1. A medical device comprising a metal complex comprising a metal and at least one ligand, at least one of the ligands being a bipyridine ligand;
   wherein the metal complex attaches to a surface of the medical device or a coating on the medical device, and
   wherein the metal complex catalyzes the in-vivo generation of nitric oxide.

2. The medical device of claim 1, wherein the in vivo generation of nitric oxide is nitric oxide generation in a blood stream or a tissue adjacent to the medical device.

3. The medical device of claim 1, wherein the coating on the medical device is present; and wherein the coating comprises a polymer to which the metal complex is attached.

4. The medical device of claim 1, wherein the medical device is a bioabsorbable stent comprising a polymer to which the metal complex is a attached.

5. The medical device of claim 1, wherein the metal of the metal complex comprises copper.

6. The medical device of claim 1, wherein the metal complex attaches to a surface of the medical device.

7. The medical device of claim 1, wherein the metal of the metal complex comprises a member of the group consisting of Cu, Co, Ni, Zn, Mn, Al, and Fe.

8. The medical device of claim 1, wherein the metal complex comprises an ion selected from the group consisting of $Cu^{2+}$, $Co^{2+}$, $Ni^{2+}$, $Zn^{2+}$, $Mn^{2+}$, $Al^{3+}$, and $Fe^{3+}$.

9. The medical device of claim 1, further comprising a drug.

10. The medical device of claim 9, wherein the drug is selected from the group consisting of paclitaxel, docetaxel, estradiol, super oxide dismutases, tacrolimus, dexamethasone, rapamycin, everolimus, 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), pimecrolimus, imatinib mesylate, midostaurin, clobetasol, bioactive RGD, CD-34 antibody, abciximab (REOPRO), and combinations thereof.

11. The medical device of claim 9, wherein the coating on the medical device is present and the coating comprises the drug.

12. The medical device of claim 11, wherein the coating comprises a polymer to which the metal complex is attached.

13. The medical device of claim 11, wherein the drug is selected from the group consisting of paclitaxel, docetaxel, estradiol, super oxide dismutases, tacrolimus, dexamethasone, rapamycin, everolimus, 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), pimecrolimus, imatinib mesylate, midostaurin, clobetasol, bioactive RGD, CD-34 antibody, abciximab (REOPRO), and combinations thereof.

14. The medical device of claim 1, which is a stent.

15. The medical device of claim 1, which is a bioabsorbable stent.

16. The medical device of claim 1, wherein the nitric oxide is released from a nitrosylated biomolecule present in a blood stream or a tissue adjacent to the medical device.

17. The medical device of claim 1, wherein the nitric oxide is released from a nitrosylated protein or an S-nitrosothiol present in a blood stream or a tissue adjacent to the medical device.

18. A method of treating a disorder in a patient comprising implanting in the patient the medical device of claim 1, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, diabetic vascular disease, and combinations thereof.

19. A method of treating a disorder in a patient comprising implanting in the patient the medical device of claim 10, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, diabetic vascular disease, and combinations thereof.

20. A method of treating a disorder in a patient comprising implanting in the patient the medical device of claim 13, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, diabetic vascular disease, and combinations thereof.

* * * * *